(12) United States Patent
Boucher et al.

(10) Patent No.: US 7,909,881 B2
(45) Date of Patent: Mar. 22, 2011

(54) FEMORAL PROSTHESIS

(75) Inventors: Florian Boucher, Hermanville sur Mer (FR); Everard Munting, Biez (BE)

(73) Assignee: Benoist Girard SAS (FR)

(*) Notice: Subject to any disclaimer, the term of this patent is extended or adjusted under 35 U.S.C. 154(b) by 283 days.

(21) Appl. No.: 12/215,043

(22) Filed: Jun. 24, 2008

(65) Prior Publication Data
US 2009/0088863 A1 Apr. 2, 2009

(30) Foreign Application Priority Data

Jul. 3, 2007 (GB) .................................. 0712867.1
Sep. 4, 2007 (GB) .................................. 0717185.3

(51) Int. Cl.
*A61F 2/32* (2006.01)
(52) U.S. Cl. ........................................................ 623/22.4
(58) Field of Classification Search ..... 623/20.32–23.15
See application file for complete search history.

(56) References Cited

U.S. PATENT DOCUMENTS

| | | | |
|---|---|---|---|
| 4,357,716 A * | 11/1982 | Brown | 606/94 |
| 5,571,203 A | 11/1996 | Masini | |
| 6,162,255 A * | 12/2000 | Oyola | 623/20.34 |
| 6,524,343 B2 | 2/2003 | Storer et al. | |
| 6,626,948 B2 | 9/2003 | Storer et al. | |
| 6,783,549 B1 | 8/2004 | Stone et al. | |
| 7,104,995 B2 | 9/2006 | Crofford | |
| 7,338,498 B2 | 3/2008 | Long et al. | |
| 2003/0125810 A1 | 7/2003 | Sullivan et al. | |
| 2003/0187514 A1* | 10/2003 | McMinn | 623/22.44 |
| 2006/0015188 A1* | 1/2006 | Grimes | 623/23.19 |
| 2008/0119942 A1 | 5/2008 | Mercuri et al. | |

FOREIGN PATENT DOCUMENTS

| | | |
|---|---|---|
| DE | 10212982 | 10/2003 |
| FR | 2674122 A1 * | 9/1992 |
| WO | 86/03962 | 7/1986 |
| WO | 92/12691 | 8/1992 |
| WO | 00/72785 | 12/2000 |

OTHER PUBLICATIONS

European Search Report, EP 08 25 2244.

* cited by examiner

*Primary Examiner* — Suzette J Gherbi
(74) *Attorney, Agent, or Firm* — Lerner, David, Littenberg, Krumholz & Mentlik, LLP

(57) ABSTRACT

A prosthetic femoral implant has a stem having a proximal end and a distal end. A circumferential collar is formed on the proximal end of the stem having a proximally facing surface in the form of a circular disc extending radially inwardly and proximally from a maximum outer circumference to a central neck region. The collar has a distally facing surface extending radially inwardly and distally at an included angle with respect to a central longitudinal axis of the neck region of between 120 and 140°. The distal surface of the collar is v-shaped and may be conical in form.

24 Claims, 2 Drawing Sheets

FEMORAL PROSTHESIS

BACKGROUND OF THE INVENTION

This invention relates to a femoral prosthesis of the type which employs a short stem. The term short stem is used herein to indicate a stem which only extends into the femur up to or slightly beyond the neck beneath the head. Short stems of this type are being developed by the Applicant to preserve bone stock for young patients.

Numerous short stem designs have been developed and used on the market over the last 50 years. Clinical results and finite element analysis have shown that most of these stems, which were designed to preserve bone stock, are in fact leading to bone resorption in proximal areas of the femur and bone formation in the distal contact area of the stem with the femur.

WO 86/03962 shows a stem of this type has been used by surgeons. Unfortunately the first generation of instrumentation was unprecise and the clinical results were poor when the stem was malpositioned on the femur (too much varus, lack of contact on proximal/medial cortex). On the other hand when the stem was well positioned the clinical results were successful and still are after 18 years clinical follow-up. It has been confirmed that the stem design keeps most of the natural stress distribution in the femur when well positioned but the problem is preventing malpositioning.

SUMMARY OF THE INVENTION

The present invention is intended to prevent the problems created in this earlier type of stem.

According to the present invention a femoral prosthesis comprises a short stem and a neck carrying a spherical bearing member and in which the neck includes a support which has a distal engagement surface adapted to engage a prepared surface on a receptive femur. The engagement surface is substantially flat, part conical or conical V-shaped with an enclosed angle of between 120° and 140°.

It has been found that keeping the natural stress fraction in the femur has been identified as a V-shape between these angles and is preferably 130°.

Preferably the stem and neck dimensions are arranged so that the engagement surface is adapted to engage the prepared surface on the resected femur at a cervico-diaphysal angle of approximately 130° and the engagement surface needs to cover the resected proximal/medial cortex which gives good results.

The distal end of a short stem is adapted to be enclosed within the femur when located therein rather than protruding through one of the side walls of the bone.

The support and the stem can both have a coating of HA (hydroxyapatite).

The stem can be relatively straight and be substantially conical or tapered. The angle of the cone or taper may between 2° and 10°.

In an alternative arrangement the short stem can be curved along its length.

If desired the stem axis can be spaced apart from the neck axis towards the medial cortex.

In another construction the stem axis can be perpendicular to the metal engagement surface and the medial part of the stem can be rounded and straight parallel to the stem axis and the lateral part can be curved.

Various aspects of the invention are provided by a method of resurfacing the proximal femur including resecting the head and neck of a proximal femur adjacent a greater trochanter thereof and forming a bore in the resected proximal femur along a central axis of the head and neck. A recessed surface is formed around the bore having surfaces forming a 120°-140° included angle relative to the head and neck central axis. A prosthetic implant is implanted into the bore and surface, the implant having a stem with a central longitudinal axis forming an angle of between 0° and 135° with a head and neck central axis of the implant. An intermediate collar portion of the implant may include a bone engagement surface having an included angle matching the surface of the proximal femur surrounding the bore for contacting therewith upon implantation. The distal surface of the collar may be v-shaped and may be conical in form and the stem may be curved. The included angle of the distally facing bone engagement surface is preferably 130°. The stem longitudinal axis can be perpendicular to a medial bone engagement surface of the collar and the apex of the angled distally facing bone engagement surface may be offset toward the medial cortex from the central longitudinal stem axis.

A preferred prosthetic femoral implant has a stem having a proximal end and a distal end. A circumferential collar is formed on the proximal end of the stem having a proximally facing surface in the form of a circular disc extending radially inwardly and proximally from a maximum outer circumference to a central neck region. The collar has a distally facing surface extending radially inwardly and distally at an included angle with respect to a central longitudinal axis of the neck region of between 120 and 140°. Thus the distal surface of the collar is v-shaped and may be conical in form. The stem is preferably curved. In the preferred prosthetic femoral component the included angle of the distally facing bone engagement surface is 130°.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

The invention can be performed in various ways and some embodiments will now be described by way of example and with reference to the accompanying drawings in which.

DETAILED DESCRIPTION

Figure 2:
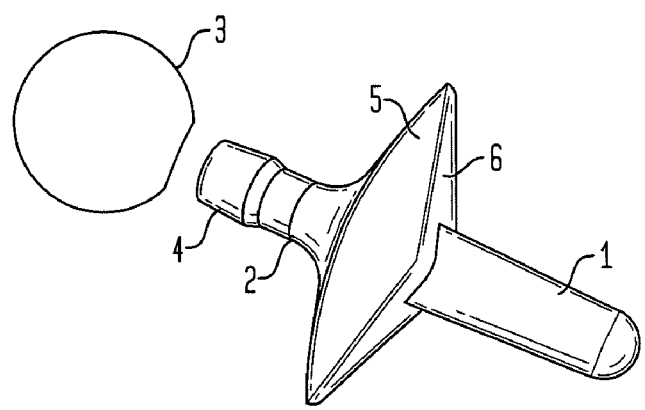
FIG. 2 is a diagrammatic side view of a prosthesis according to the invention.
Figure 4:
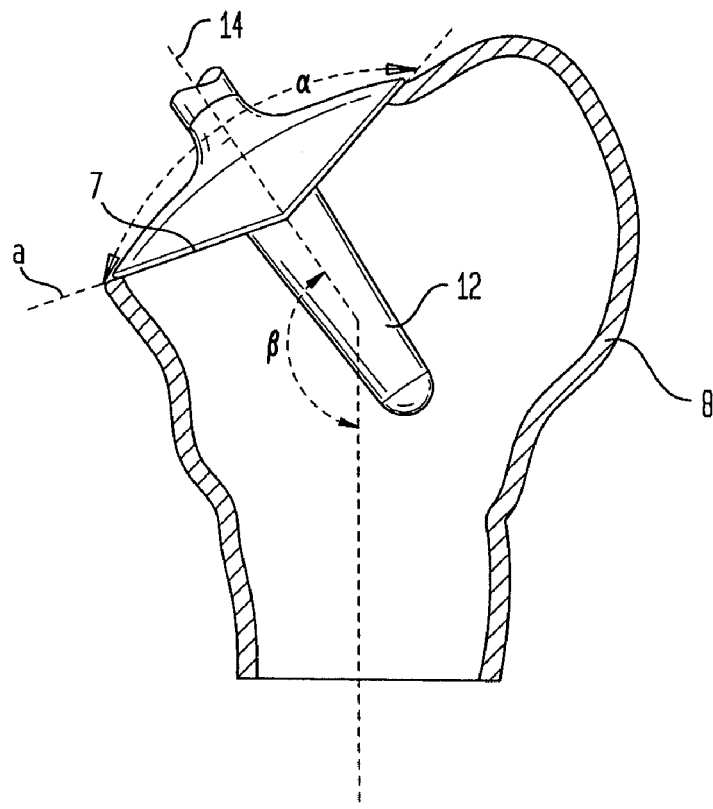
FIG. 4 is a diagrammatic side view of a resected femur prepared to receive the prosthesis.

A first preferred embodiment of the invention is shown in FIG. 2 and comprises a femoral prosthesis having a short stem 1 and a neck 2 carrying a spherical bearing member 3. The bearing member 3 can be engaged on a morse taper 4 provided on the stem 2 as is well known in the art. The neck 2 includes a support 5 which has a distal engagement surface 6 adapted to engage a prepared surface 7 on a resected femur 8 as shown in FIG. 4.

The engagement surface 6 on the support 5, in this construction, is V-shaped with substantially flat surfaces. If desired the surfaces could be slightly curved or part-conical and the prepared surface 7 on the femur is appropriately shaped to receive them. The enclosed angle between the surfaces 6 is between 120° and 140° and is preferably 130°.

The stem and neck dimensions are arranged so that the engagement surface 6 is adapted to engage the prepared surface 7 on the resected femur at a cervico-diphysal angle of approximately 130°.

Figure 1:
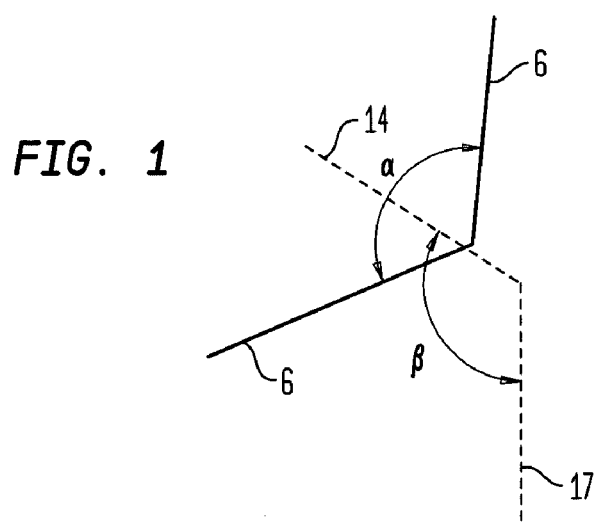
FIG. 1 is a diagram showing the angles of the engagement surface on the support in relation to a cervico-diaphysal angle of the bone.

The relative angle is shown in FIG. 1, the enclosed angle between the surfaces 6 is represented by the Greek letter α and the cervico-diphysal angle is indicated by Greek letter β. The angles are also shown on FIG. 4 in relation to the resected femur 8, the cervico-diphysal angle β is the angle between the neck axis 14 and the axis 17 of the femur 8.

The surfaces 6 and the stem 1 are HA coated and the short stem goes into the proximal spongy bone of the femur. This conical or tapered short stem with a conical or tapered angle of between 2° to 10° will create a morse tapered retentive effect in the spongious bone for initial stability.

A prepared special instrument smaller than the short stem but with the same geometry will help compacting spongious bone in order to create an optimal press-fit between the compacted spongy bone and the HA coated short stem.

Another prepared reamer can be used to create an over reamed canal at the tip of the short stem in order to avoid distal contact of the stem with bone of the tip and bone formation there at the same time providing optimum contact and load transfer between the engagement surface 6 and the prepared surface 7.

The HA coated distal facing V-shape of 130° at a cervico-diaphysal angle of approximately 130° creates conditions for natural stress distribution in the femur and the short stem press-fitted into the compacted spongy bone provides initial stability to the implant. The short stem with a conical or tapered angle of 2° to 10° press-fitted into the compacted spongy bone also provides initial stability to the implant.

This design is simpler and easier to employ than the system shown in WO 86/03942. The instrumentation is also more simple and precise and the same entrance can be used for left or right femurs.

Figure 3:
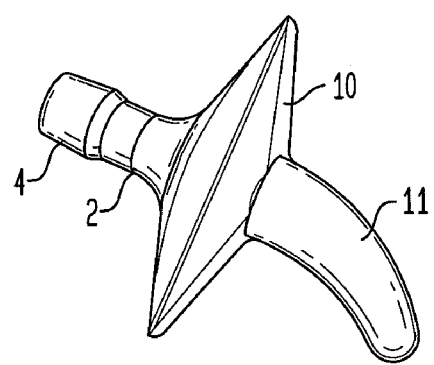
FIG. 3 is a diagrammatic side view of an alternative construction of a femoral prosthesis according to the invention.

In this construction a stem of any suitable shape can be used, for example a curved stem of the type shown in FIG. 3 to be described herein.

FIG. 3 shows another construction according to the invention in which the same reference numerals are used to indicate similar parts. In FIG. 3 the spherical bearing member is not shown but can be similar to that shown in FIG. 2.

In FIG. 3 the V-shaped bearing surfaces 6 are replaced by a conically inwardly tapered V-shaped bearing surface 10 and the straight stem 1 is replaced by a downwardly curved stem 11.

The resected femur 8 is prepared in a similar way to that for the construction shown in FIG. 2 and again the bearing surface 10 is adapted to mate with the prepared surface 7. If desired the curved stem could be replaced by an upwardly curved stem or a straight stem 1 could be used in place of the curved stem 11 or a stem of any other convenient shape.

In FIG. 4 the prepared opening 12 to receive the stem 1 or 11 is shown and is arranged so that the whole of the stem is enclosed within the bone and does not extend beyond its outer surfaces.

Figure 5:
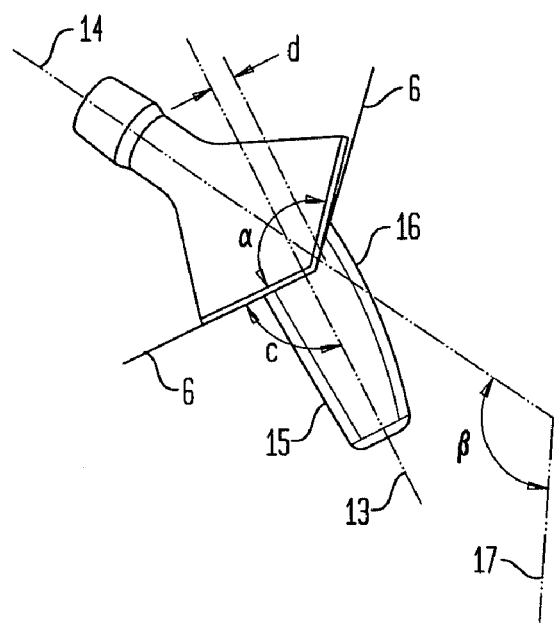
FIG. 5 is a diagrammatic side view of another alternative construction according to the invention.

FIG. 5 shows an alternative construction in which the short stem axis 13 is perpendicular to the medial engagement surface 6 and which is indicated by reference letter c which, in this embodiment, is 90°. The intention is to preserve bone stock of a proximal femur and to facilitate stem insertion while keeping optimum contact and load transfer between the engagement surface 6 and the prepared bone surface 7 (not shown in FIG. 5).

Short stem insertion into the femur 8 is made following the direction of stem axis 13 and which is at a distance offset from the neck axis 14 towards the medial cortex to preserve even more bone stock of the proximal femur. This displacement is indicated by reference numeral d in FIG. 5.

The medial part of the short stem 15 is rounded and straight, parallel to the short stem axis 13 to facilitate short stem insertion and the lateral part of the short stem 16 is curved to preserve even more bone stock and to increase its initial stability into the femur 8.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of resurfacing the proximal femur comprising:
   resecting the head and neck of a proximal femur adjacent a greater trochanter thereof;
   forming a bore in the resected proximal femur along a central axis of the head and neck;
   forming a recessed surface around the bore having surfaces forming a 120°-140° included angle relative to the head and neck central axis; and
   implanting a prosthetic implant into the bore and surface, the implant having a stem with a central longitudinal axis forming an angle of between 0° and 135° with a head and neck central axis of the implant, an intermediate collar portion of the implant including a bone engagement surface having an included angle matching the surface of the proximal femur surrounding the bore for contacting therewith upon implantation.

2. The method as set forth in claim 1 wherein the distal surface of the collar is v-shaped.

3. The method as set forth in claim 1 wherein the distal surface is conical in form.

4. The method as set forth in claim 1 wherein the stem is curved.

5. The method as set forth in claim 1 wherein the included angle of the distally facing bone engagement surface is 130°.

6. The method as set forth in claim 2 wherein the stem longitudinal axis is perpendicular to a medial bone engagement surface of the collar.

7. The method as set forth in claim 6 wherein the apex of the angled distally facing bone engagement surface is offset toward the medial cortex from the central longitudinal stem axis.

8. A prosthetic femoral implant comprising a curved stem having a proximal end and a distal end;
   a circumferential collar formed on the proximal end of the stem having a proximally facing surface in the form of a circular disc extending radially inwardly and proximally from a maximum outer circumference to a central neck region and having a distally facing surface extending radially inwardly and distally at an included angle with respect to a central longitudinal axis of the neck region of between 120 and 140° a-wherein the stem and neck dimensions are arranged so that the engagement surface engages the prepared surface on the resected femur at a cervico-diaphysal angle of between 125° and 140°.

9. The prosthetic femoral implant as set forth in claim 8 wherein the distal surface of the collar is v-shaped.

10. The prosthetic femoral implant as set forth in claim 9 wherein the distal surface is conical in form.

11. The prosthetic femoral component as set forth in claim 8 wherein the included angle of the distally facing bone engagement surface is 130°.

12. A femoral prosthesis comprising a short stem and a neck carrying a spherical bearing member and in which said neck includes a support which has a distal engagement surface to engage a prepared surface on a resected femur, said engagement surface being substantially flat, part conical or conical v-shape with an enclosed angle of between 120° and 140°, wherein the stein and neck dimensions are arranged so that the engagement surface engages the prepared surface on the resected femur at a cervico-diaphysal angle of between 125' and 140'.

13. The femoral prosthesis as claimed in claim 12 in which the enclosed angle is 130°.

14. The femoral prosthesis as set forth in claim 12 in which the cervico-diaphysal angle is 135°.

15. The femoral prosthesis as set forth in claim 12 in which the distal end of said stem is adapted to be enclosed within the femur when located therein.

16. The femoral prosthesis as set forth in claim 12 in which the support has a coating of HA.

17. The femoral prosthesis as set forth in claim 12 in which the stem has a coating of HA.

18. The femoral prosthesis as set forth in claim 12 in which the short stem is substantially conical to provide a taper of between 3° to 10°.

19. The femoral prosthesis as claimed in claim 12 in which the short stem is curved along its length.

20. The femoral prosthesis as claimed in claim 12 in which the stem axis is spaced apart from the neck axis toward the medial cortex.

21. The femoral prosthesis as claimed in claim 12 in which the stem axis is perpendicular to the engagement surface and the medial part of the stem is rounded and straight parallel to the stem axis and the lateral part of the stem is curved.

22. A femoral prosthesis comprising a short stem and a neck carrying a spherical bearing member and in which said neck includes a support which has a distal engagement surface to engage a prepared surface on a resected femur, said engagement surface being substantially flat, part conical or conical v-shape with an enclosed angle of between 120° and 140° in which the short stem is curved along its length.

23. A femoral prosthesis comprising a short stem and a neck carrying a spherical bearing member and in which said neck includes a support which has a distal engagement surface to engage a prepared surface on a resected femur, said engagement surface being substantially flat, part conical or conical v-shape with an enclosed angle of between 120° and 140° in which the stem axis is spaced apart from the neck axis toward the medial cortex.

24. A femoral prosthesis comprising a short stem and a neck carrying a spherical bearing member and in which said neck includes a support which has a distal engagement surface to engage a prepared surface on a resected femur, said engagement surface being substantially flat, part conical or conical v-shape with an enclosed angle of between 120° and 140° in which the stem axis is perpendicular to the engagement surface and the medial part of the stem is rounded and straight parallel to the stem axis and the lateral part of the stem is curved.

* * * * *

UNITED STATES PATENT AND TRADEMARK OFFICE
CERTIFICATE OF CORRECTION

PATENT NO.        : 7,909,881 B2
APPLICATION NO.   : 12/215043
DATED             : March 22, 2011
INVENTOR(S)       : Florian Boucher and Everard Munting It is certified that error appears in the above-identified patent and that said Letters Patent is hereby corrected as shown below:

On the Title Pg, under Abstract Item (57), line 9, "120" should read --120°--.
Column 1, line 6, "term short stem is" should read --term "short stem" is--.
Column 1, line 21, "the other hand when" should read --the other hand, when--.
Column 1, line 25, "positioned but the" should read --positioned, but the--.
Column 2, line 28, "120" should read --120°--.
Column 5, line 1, "120 and 140° a-wherein" should read --120° and 140° wherein--.
Column 5, line 21, "125' and 140'." should read --125° and 140°.--.

Signed and Sealed this
Sixth Day of March, 2012

David J. Kappos
*Director of the United States Patent and Trademark Office*